United States Patent
Chevigny et al.

(10) Patent No.: US 8,114,809 B2
(45) Date of Patent: Feb. 14, 2012

(54) POLYSACCHARIDE-INORGANIC COMPOSITE PARTICLES AS PERFORMANCE ADDITIVES FOR SUPERABSORBENT POLYMERS

(75) Inventors: Stéphane Chevigny, Varennes (CA); Shuojia Dong, Montreal (CA); Anne-Claude Couffin-Hoarau, Montreal (CA); Isabelle Bolduc, Chambly (CA); Mohammed Berrada, Longueuil (CA); Claude Thibodeau, Napierville (CA)

(73) Assignee: Archer Daniels Midland Company, Decatur, IL (US)

( * ) Notice: Subject to any disclaimer, the term of this patent is extended or adjusted under 35 U.S.C. 154(b) by 900 days.

(21) Appl. No.: 11/814,653

(22) PCT Filed: Jan. 26, 2006

(86) PCT No.: PCT/CA2006/000136
§ 371 (c)(1),
(2), (4) Date: Jun. 27, 2008

(87) PCT Pub. No.: WO2006/079221
PCT Pub. Date: Aug. 3, 2006

(65) Prior Publication Data
US 2008/0261807 A1    Oct. 23, 2008

(30) Foreign Application Priority Data

Jan. 26, 2005    (CA) .................................. 2495473

(51) Int. Cl.
*B01J 20/00* (2006.01)
(52) U.S. Cl. ........................... 502/404; 502/439
(58) Field of Classification Search .................. 502/401, 502/403–407, 413, 416, 417, 439, 526
See application file for complete search history.

(56) References Cited

U.S. PATENT DOCUMENTS 4,454,055 A  *  6/1984  Richman et al. .............. 252/194

FOREIGN PATENT DOCUMENTS

| CA | 2405618 | * | 4/2001 |
| CA | 2483049 | * | 9/2005 |
| EP | 0087001 | * | 1/1995 |

* cited by examiner

*Primary Examiner* — Edward Johnson
(74) *Attorney, Agent, or Firm* — Mark W. Roberts

(57) ABSTRACT

The present invention relates to discrete particulate composite additives for superabsorbent polymers and includes a method of making same. The discrete particulate composite additives generally comprise a polysaccharide and an inert inorganic component. Advantageously, these discrete particulate composite additives functionally improve superabsorbent performance. They are suitable for a number of applications, including the use and manufacture of hygiene products.

21 Claims, 5 Drawing Sheets

POLYSACCHARIDE-INORGANIC COMPOSITE PARTICLES AS PERFORMANCE ADDITIVES FOR SUPERABSORBENT POLYMERS

CROSS REFERENCE TO RELATED APPLICATIONS

The present application is a national phase application under 35 U.S.C. §371 of International Application No. PCT/CA2006/000136, filed 26 Jan. 2006, which claims the benefit of Canadian Application No. 2,495,473, filed 26 Jan. 2005. The entire text of these applications are incorporated by reference.

FIELD OF THE INVENTION

The present invention relates to additives that improve the performance of superabsorbent polymers. The invention further includes the use of such additives as well as means for producing same.

BACKGROUND OF THE INVENTION

Superabsorbent polymers can be employed in various applications, such as in disposable sanitary products (i.e. diapers, incontinence articles, feminine hygiene products, and absorbent dressings), airlaids, household articles, sealing materials, humectants (i.e. agricultural products for soil conditioning), mining and oil drilling, anti-condensation coatings, water-storing materials (for use in fields as diverse as agriculture, horticulture and forestry), absorbent paper products, surgical absorbents, pet litter, bandages, wound dressings, chemical absorbents, polymeric gels for cosmetics and pharmaceuticals, artificial snow, in fire-fighting techniques, and in applications related to the transportation of fresh food or seafood, as well as in food packaging applications.

The largest use of superabsorbent materials or polymers (also referred to as SAP), however, is in disposable personal hygiene products. These products include, in the order of volume of superabsorbent materials used, diapers, training pants, adult incontinence products and feminine hygiene products.

Superabsorbent polymers and fluff cellulose pulp are usually mixed uniformly in diapers and incontinence products. This mixture of fluff and superabsorbents is formed in absorbent structures called "absorbent cores". Unfortunately, physiological fluids are excreted and absorbed over only a small area of these absorbent cores. The superabsorbent performance of these absorbent cores is therefore not optimal.

Fluid acquisition or fluid distribution layers have been added to diapers and incontinence garments for some time. (See, for example, U.S. Pat. No. 5,137,600 (Barnes et al).) These nonwoven textiles increase liquid diffusion along the length and width of absorbent structures (i.e., along the X and Y axes), and in this way increase the amount of superabsorbents that is placed in contact with fluids. However, nonwoven textiles do not enhance the performance of superabsorbents. Nonwoven textiles can only be placed at the surface of absorbent structures, and this minimizes their impact on liquid penetration through the absorbent structures (i.e., along the Z axis). Furthermore, they are usually very expensive. Due to their high cost, fluid distribution layers are usually placed over a small area in absorbent structures and thus have only a limited effect on liquid diffusion.

Superabsorbent polymers (SAP) can be mixed with inorganic additives, such as clays, zeolites or silicates. Several additives have been mixed with superabsorbent polymers or in hygiene products for odor control purposes. (See, for example, U.S. Pat. No. 6,225,524 and European Patent No. 0751 791 (Guarracino et al); U.S. Pat. No. 6,096,299; International Patent Application No. WO 91/12031 (Ryan et al); International Patent Application Nos. WO 99/30754 and 99/30752 (Carlucci et al); U.S. Pat. No. 5,980,879 (Hiroki et al); Japanese Patent No. 04-114741 (Takahashi et al); U.S. Pat. No. 6,175,055 (Schöne); International Patent Application No. WO 91/11977 (Furio et al); International Patent Application No. WO 81/01643 (Dodwel et a) and U.S. Pat. No. 4,826,497 (Marcus et al). However, not all of these additives were reported to improve superabsorbent performance in diapers or incontinence garments.

Wong et al (United States Patent Application No. 2003/131,799), Brehm et al (United States Patent Application No. 2003/158,296 and U.S. Pat. No. 5,248,709) and Brüggeman et al (U.S. Pat. Nos. 5,847,031 and 5,721,295) describe absorbent polymer compositions made from matrix bound (melt bound) particles of superabsorbent polymers and additives. The additives are either polysaccharides or clays. As described in Pietsch (*Agglomeration Processes: Phenomena, Technologies, Equipment*, Wiley-VCH, 2002, ISBN 3-527-30369-3, at page 44), matrix forming binder components fill entire pore spaces, and therefore drastically reduce porosity and accessible surface area. High specific surface areas and porosity provide higher driving forces for fluid transport through the absorbent structure, as demonstrated by Roe (U.S. Pat. No. 5,419,956).

Superabsorbent material was also reported to play a role as a matrix material or binder. Hiroki et al (U.S. Pat. No. 5,980,879) teaches that superabsorbent particles occlude odor control additives, such as zeolites. Jiro et al (Japanese Patent No. 59-008711) and Herfert et al (United States Patent Application No. 2005/239,942) describe superabsorbent particles that occlude additives, such as clays, alumina or silica. Suskind et al (U.S. Pat. Nos. 5,539,019 and 5,849,816) discuss solid cores covered with absorbent polymers. Murukami et al (U.S. Pat. No. 4,418,163) and Herfert et al (United States Patent Application No. 2005/245,393) are concerned with superabsorbents coated with inorganic particles (clay, calcium carbonate, magnesium silicate, barium sulphate). Kobayashi et al (U.S. Pat. No. 5,489,469) and Sears (U.S. Pat. No. 6,855,182) describe composites made from fibers, swollen absorbent polymers and water insoluble inorganic materials, such as alumina, silica, zeolite and clays. The absorbent materials will therefore fill pore spaces, drastically reducing accessible surface area.

Takahashi et al (Japanese Patent No. 04-114741), Chmelir et al (European Patent No. 0318989), Obayashi et al (U.S. Pat. No. 4,732,968), Yanagisawa et al (Japanese Patent No. 08-010616) and Woodrum et al (U.S. Pat. No. 4,914,066) report agglomerated particles made from silicates and fine superabsorbent particles. Takai et al (U.S. Pat. No. 6,284,362) is concerned with agglomerated particles made from metal oxides and fine superabsorbent particles. Reeves et al (U.S. Pat. No. 6,387,495), Skidmore et al (International Patent Application No. WO 00/16816), Luke et al (U.S. Pat. No. 5,609,123) and Toth et al (U.S. Pat. No. 5,339,769) teach agglomerated particles made from clays and fine superabsorbent particles. Yen et al (U.S. Pat. No. 3,900,378) describe agglomerated particles made from diatomaceous earth, clay or magnesium silicate and fine superabsorbent particles. As reported by Berg et al (U.S. Pat. No. 5,300,565) water-agglomerated superabsorbent fine particles dissociate upon contact and/or swelling with an aqueous solution. This results in a concentration of swollen free fine particles that will contribute to an increased gel blocking.

McKinley et al (U.S. Pat. No. 4,500,670), Duchane (U.S. Pat. No. 3,932,322) and Tsubakimoto et al (U.S. Pat. Nos. 4,734,478 and 4,286,082) describe optimized superabsorbents mixed with additives, such as silica, diatomaceous earth and clays. As discussed in Roe (U.S. Pat. No. 5,419,956), none of the foregoing appears to have adequately understood and addressed the problems associated with the transport rate of fluids in both the X-Y plane and in the Z-direction. Moreover, these additives are not made from organic components.

Kodaira et al (Japanese Patent No. 01-004653) and Sun et al (U.S. Pat. No. 6,124,391) report superabsorbent compositions comprising inorganic substances, especially kaolin. Sun emphasizes anti-caking effects of inorganic substances, but also demonstrates improved SAP performances attributed to the inorganic component. However, Sun and Kodaira don't describe additives made from organic components.

Biodegradability and sustainable development issues were raised recently in the superabsorbent industry when increases in oil prices created provisioning problems (Kuster B., Nonwovens World, December-January 2005, p. 57). One solution to the "SAP shortage" was to propose a reduction of the SAP content in hygiene articles. However, this strategy does not necessarily involve SAP optimization.

As alternatives, the Groupe Lysac proposed many absorbent compositions made from biodegradable and renewable feedstocks. (See, for example, Canadian Patent No. 2,308,537 (Huppé et al); Canadian Patent No. 2,362,006 (Couture et al); Canadian Patent No. 2,426,478 (Bergeron); Canadian Patent No. 2,462,053 (Thibodeau et al); and Canadian Patent No. 2,483,049 (Berrada et al).) However, these patents do not relate to additives that have the effect of improving the performance of superabsorbents.

Takahiro et al (Japanese Patent No. 01-296933), Marx (U.S. Pat. No. 4,615,923) and Brander et al (U.S. Pat. No. 6,376,034) describe inorganic additives (kieselguhr, clays, diatomaceous earth) added to biodegradable superabsorbents. However, none of these patents teach additives made from organic components.

Richman et al (U.S. Pat. No, 4,454,055) and Spence (U.S. Pat. No. 4,272,514) report the use of starch, a natural and biodegradable polymer, as an additive for superabsorbent polymers. Richman and Spence also teach the use of inorganic additives for enhancing the performance of superabsorbent polymers. However, neither Richman nor Spence describes the use of both organic (starch) and inorganic components in a single particle.

There thus remains a need for an additive that effectively improves the performance of superabsorbents. Ideally, such an additive would be cost-efficient and be composed of mainly renewable resources. Moreover, the additive would combine synergistically, in a single particle, organic components as well as inorganic components.

The present invention seeks to meet these and other needs.

The following description refers to a number of documents, the contents of which are herein incorporated by reference in their entirety.

SUMMARY OF THE INVENTION

The present invention relates to novel composite functional additives. These additives are composed of discrete particles that are suitable to be blended with superabsorbent polymers and that improve superabsorbent performance. These discrete particles are generally comprised of a polysaccharide and an inorganic component.

In one embodiment, the present invention is concerned with superabsorbent compositions comprising a superabsorbent polymer and a composite additive.

The present invention further includes hygiene articles comprising the absorbent composition, as well as a process for the manufacture of the additive. Non limiting examples of means for making the additive of the present invention include tumble growth agglomeration, pressure agglomeration and matrix melt formation.

In another embodiment, the present invention concerns the use of the absorbent composition for the absorption of fluids. The absorbent compositions would be used to absorb fluids including but not limited to water, aqueous solutions, saline solutions and physiological solutions.

Other objects, advantages and features of the present invention will become more apparent upon reading of the following non restrictive description of embodiments thereof, given by way of example with reference to the accompanying figures.

DETAILED DESCRIPTION OF THE INVENTION

Figure 1:
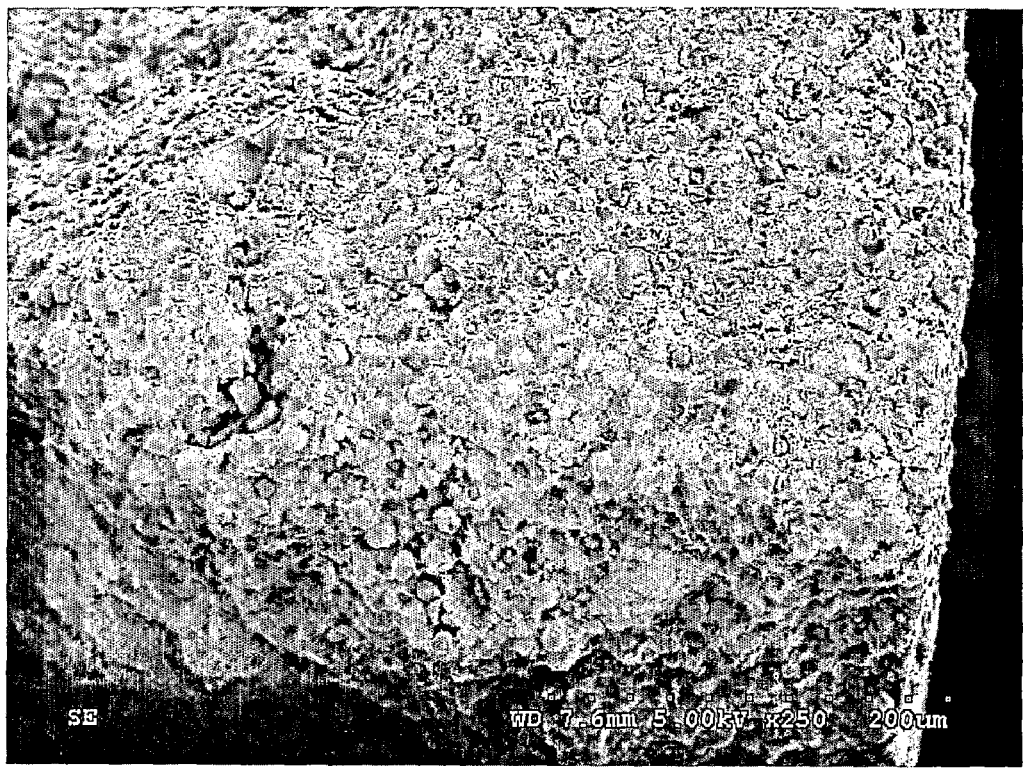
FIG. 1 illustrates a scanning electron micrograph (Magnification 250 times) of an agglomerated composite additive according to an embodiment of the present invention.

In order to provide a clear and consistent understanding of the terms used in the present specification, a number of definitions are provided below. Additionally, the present description refers to a number of routinely used chemical and technical terms. Unless otherwise defined, the terms used in the present description have the meanings that would be understood by one of skill in the art.

DEFINITIONS

The use of the word "a" or "an" when used in conjunction with the term "comprising" in the claim(s) and/or the specification may mean "one", but it is also consistent with the meaning of "one or more", "at least one", and "one or more than one". Similarly, the word "another" may mean a second or more.

The words "comprising" (and any form comprising, such as "comprise" and "comprises"), "having" (and any form of having, such as "have" and "has"), "including" (and any form of including, such as "include" and "includes"), or "containing" (and any form of containing, such as "contain" and "contains"), are inclusive or open-ended. They do not exclude additional, unrecited elements or method steps.

The term "about" is used to indicate that a value includes an inherent variation of error for the device or the method being employed to determine the value.

As used herein, the term "percent" or "%" refers to percentages in weight (W/W).

As used herein, the term "additive for superabsorbent polymers" refers to a substance, added to superabsorbent polymer, in contents up to 50% (w/w). Such a substance may be a composite according to the present invention which is added to a superabsorbent but does not exceed more than 50% of the absorbent composition.

As used herein, the term "discrete particle" refers to individual particles.

As used herein, the term "superabsorbent polymers" also called "SAP", refers to hydrogel forming absorbent polymers having a Centrifuge Retention Capacity (CRC) of at least 15 g/g. These superabsorbent polymers are best when dry and in the form of discrete particles.

As used herein, the term "discrete additive particles for superabsorbent polymers" refers to individual additive particles which are added to individual superabsorbents.

As used herein, the term "functional additive for superabsorbent polymers" refers to additives for superabsorbent polymers which, by their action, will improve superabsorbent performances. This improvement may be determined with the absorbent compositions or directly in hygiene articles. Non-limiting examples of improved characteristics for superabsorbent particles that may evaluated are higher free swell capacity, higher centrifuge retention capacity, higher absorption under load and lower particle rewet. Non-limiting examples of improved characteristics in hygiene articles are lower rewet, lower penetration time and higher stain area.

As used herein, the term "composite particle" refers to particles made from two or more constituent materials that remain distinct on a micrometric level while forming a single particle.

As used herein, the term "polysaccharide" refers to polymers comprising a backbone comprised mainly of (at least 90%) monosaccharide repeating units and/or derivatized monosaccharide repeating units. Non-limiting examples include starches, modified starches, amylopectin, modified amylopectin, amylose, modified amylose, chitosan, chitin, guar gum, modified guar gum, locust bean gum, tara gum, konjac gum, konjac flour, fenugreek gum, mesquite gum, aloe mannans, cellulose, modified cellulose (representative examples include carboxyalkylated cellulose and carboxymethyl cellulose), oxidized polysaccharides, sulfated polysaccharides, cationic polysaccharides (such as, but not limited to, the chitosan, quaternary ammonium derivatives of polysaccharides or guanidinated polysaccharides, as described in Canadian Patent No. 2,519,417 (Berrada)), pectin, arabic gum, karaya gum, xanthan, kappa, iota or lambda carrageenans, agar-agar, alginates and mixture thereof.

As used herein, the term "monosaccharide unit", refers to cyclic $C_5$-$C_6$ aldoses or ketoses. Non limiting examples of $C_5$-$C_6$ aldoses include allose, altrose, glucose, mannose, gulose, idose, galactose, talose, ribose, arabinose, xylose, lyxose. Non limiting examples of $C_5$-$C_6$ ketoses include ribulose, xylulose, fructose, sorbose and tagatose.

As used herein, the term "monosaccharide derivatives" refers to any chemically or enzymatically modified monosaccharide unit.

As used herein, the term "inorganic material" refers to materials which are not member of a large class of chemical compounds whose molecules contain carbon.

As used herein, the term "inert inorganic material" refers to inorganic materials which will not significantly react chemically or dissolve in water.

As used herein, the term "swelling clay" refers to clays which will be able to swell in deionized water. Non-limiting examples of such clays are smectites, hectorites, bentonites, montmorillonites, Laponites™, celites, illites and mixture thereof.

As used herein, the term "molten polysaccharides" refers to polysaccharides for which a sufficient amount of water and heat has been provided to break their native crystalline pattern. A synonymous term, "gelatinized", is often used when referring to starch.

As used herein, the term "agglomerated composite" refers to the morphology of composite particles, wherein the polysaccharide and the inorganic component are discrete particles bound together.

As used herein, the term "uniform composite" refers to the morphology of composite particles, wherein the polysaccharide is a uniform amorphous polysaccharide occluding the inorganic components.

Figure 3:
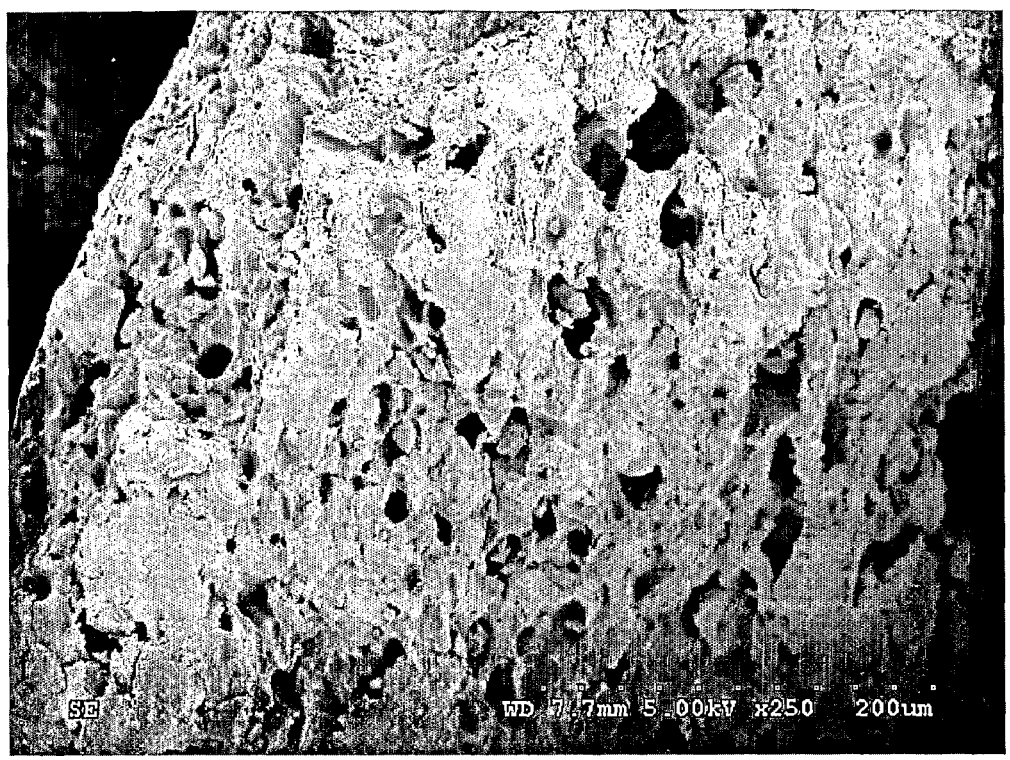
FIG. 3 illustrates a scanning electron micrograph (Magnification 250 times) of a semi-uniform composite additive, according to another embodiment of the present invention.
Figure 4:
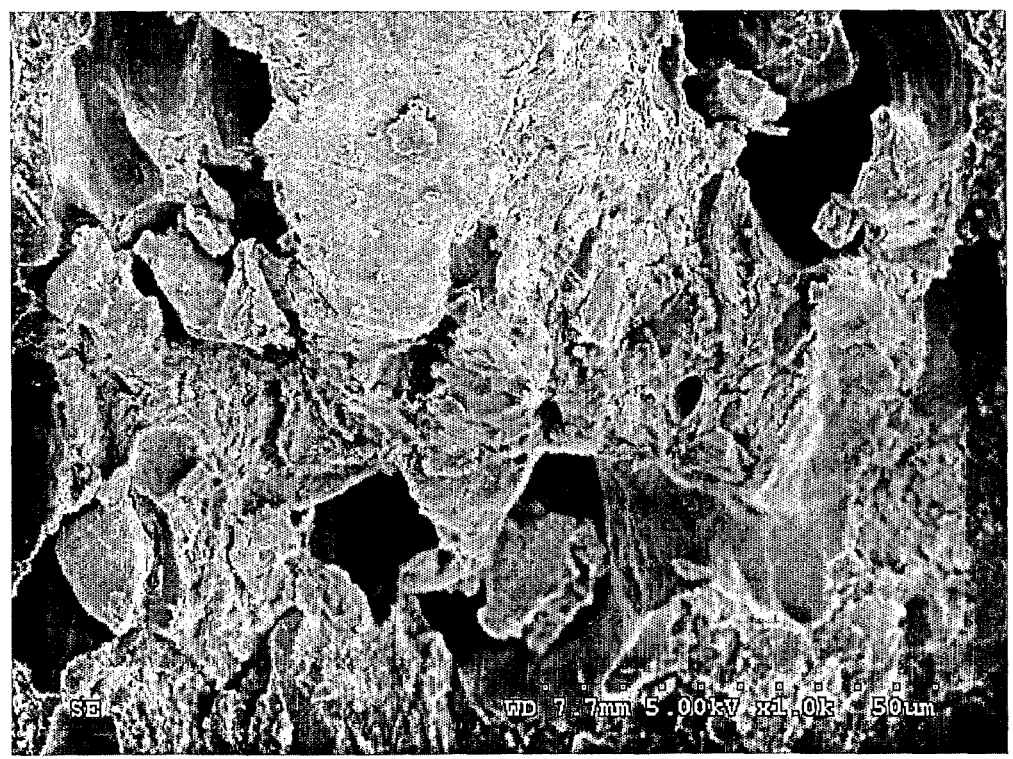
FIG. 4 illustrates a scanning electron micrograph (Magnification 1,000 times) of the semi-uniform composite additive shown in FIG. 3.

As used herein, the term "semi-uniform composite" refers to the morphology of composite particles, wherein the polysaccharide comprises uniform and agglomerated morphologies. This morphology could be very specific and exhibit various shapes, such as sponge-like designs, as shown in FIGS. 3 and 4.

As used herein, the term "discrete blending" or "discrete blend" refers to a process wherein the additive is mixed with a superabsorbent polymer, but wherein both the superabsorbent polymer and the additive particles retain their discrete characters.

As used herein, the term "Liquid-SAP ratio" refers to the amount of saline solution that is used, for example, in a hygiene article or poured in a particle rewet test, per gram of a given superabsorbent polymer. Liquid-SAP ratio higher than CRC of the given SAP will exhibit interstitial water between SAP particles; while a liquid-SAP ratio lower than CRC of the given SAP will exhibit partially swollen SAP.

As used herein, the term "Free Swell Capacity" (FSC), also called "Total Absorption", refers to the amount (g) of fluid absorbed per gram of the composition. A typical fluid used for this determination is saline solution (0.9% Weight/Weight NaCl solution, hereinafter called 0.9% NaCl solution or saline).

As used herein, the term "Centrifuge Retention Capacity" (CRC), also called "Retention", refers to the amount (g) of fluid retained per gram of the composition, following exposure of the composition to a centrifugation force of 250 G. A typical fluid used for this determination is saline solution (0.9% NaCl solution or saline).

As used herein, the term "Absorption Under Load" (AUL) at 0.3 PSI, 0.7 PSI or 0.9 PSI, also called "Absorption Against Pressure" (AAP), refers to the amount (g) of fluid absorbed per gram of the composition under a given applied pressure. A typical fluid used for this determination is saline solution (0.9% NaCl solution or saline).

As used herein, the term "particle rewet" or "powder rewet" refers to the amount of fluid released under an applied pressure (0.7 PSI) for a given amount of superabsorbent material.

As used herein, the term "rewet" or "wet-back" refers to a physical characteristic of hygiene articles, such as a diaper, a sanitary napkin, an airlaid, a C-Fold, an absorbent core or an incontinence-garment, and is a measure of the capacity of these absorbent products to retain fluids under applied pressure (0.7 PSI).

As used herein, the term "stain area" or "diffusion" refers to a physical characteristic of hygiene articles, such a diaper, a sanitary napkin, an airlaid, a C-fold, an absorbent core or an incontinence garment, and is a measure of the staining area ($cm^2$) produced for a given amount of a liquid.

As used herein, the term "penetration time" or "acquisition time" refers to a physical characteristic of hygiene articles, such as a diaper, a sanitary napkin, an airlaid, a C-fold, an absorbent core or an incontinence garment, and is a measure of the time taken by an absorbent product to absorb a given amount of a liquid.

As used herein, the term "airlaid" refers to a type of absorbent core, usually located inside sanitary napkins and baby diapers. Airlaids are manufactured using cellulose "fluff" fibers. However, they can also be manufactured using, in addition to fluff, absorbent or superabsorbent materials, and/or bi-component fibers. Airlaids are generally made using an air-suspension of particles and fibers which are forcibly deposited on a vacuumed screen. The deposit is then compressed, resulting in an airlaid.

As used herein, the term "C-fold" refers to a type of absorbent core, usually located inside sanitary napkins, which is manufactured using an airlaid (see Canadian Patent 2,483,049 (Berrada et al)). The interior spacing of the "C-fold" usually comprises superabsorbent polymers or a superabsorbent composition.

As used herein, the term SEM refers to Scanning Electron Microscopy.

In a broad sense, the present invention relates to novel additives improving superabsorbent performances. More specifically, the present invention relates to discrete additive particles for superabsorbent polymers. Yet more specifically, the additive particles are composite particles, comprising a polysaccharide and an inert inorganic component. In an embodiment of the present, the additive of the present invention is a functional additive, improving superabsorbent polymer characteristics.

The polysaccharide part of the composite will provide biodegradability and renewability. Therefore, the polysaccharide content in the composite will be relatively high, ranging from about 40 to about 90%. The polysaccharide may be crystalline or amorphous. If the polysaccharide is crystalline, it is preferably comprised in the composite in a particle state.

Yet more specifically, polysaccharides that are suitable for use in the composite particle may be selected from the following non-limited group: starches, modified starches, amylopectin, modified amylopectin, amylose, modified amylose and mixture thereof. Amongst these polysaccharides, starch is frequently chosen as a polysaccharide for use in the agglomerated particle. Nonlimiting examples of such starches are starch granules, pregelatinized starches, glass-like starches, waxy starches, anionic starches, cationic starches, fractionated starches, cross-linked starches, hydroxyalkylated starches, alkylated starches and mixture thereof.

Starch that is suitable for the present invention may be obtained from many sources, including but not limited to wheat, maize, buckwheat, potato, cassava, sorghum, millet, oat, arrowroot, barley, beans, peas, rice, rye, waxy starches and mixture thereof. A commonly used starch is wheat starch.

Naturally occurring starch is usually organized in a semi-crystalline, water insoluble pattern, which is sometimes referred to as a "starch granule". The form of these starch granules is characteristic of their botanical origin, and their mean particle size may range from about 1 μm to about 60 μm.

Another part of composite additives of the present invention is the inert inorganic component. The inert inorganic component will provide porosity and will drive the water more efficiently through the superabsorbent polymer. The typical inert inorganic component content ranges from about 1% to about 40%. The particle size of the inert inorganic component ranges from about 10 μm to about 150 μm. Water adsorbents, such as molecular sieves, zeolites, clays, silicates, silica gel, insoluble salts and mixture thereof may preferably be used. Among this class, swelling clays may also be used.

Non limiting examples of inert inorganic substances are calcium sulfate, silica gel, zeolites and mixtures thereof. Gypsum is a good source of calcium sulfate. Clinoptilolite is a good source of zeolites. Non-limiting examples of swelling clays are smectites, hectorites, bentonites, montmorillonites, Laponites™, celites, illites and mixture thereof. Bentonite has been found to be quite suitable.

The composite of the present invention may have multiple morphologies. The composite may be uniform, semi-uniform or agglomerated. Each morphology will exhibit its own behavior and will act differently on the performances of the superabsorbent. A uniform composite will result in increases in FSC and CRC.

Process conditions will strongly influence morphology of the composite additives. The composites of the present invention may be formed by pressure agglomeration, tumble growth agglomeration or matrix melt formation.

In order to obtain composite additive particles, the polysaccharide and the inorganic component are uniformly blended together before they will be bound to each other. An agglomerating agent or a binder may optionally be mixed with other components, Non-limiting examples of suitable binders are gelling polysaccharides, such as sodium carboxymethyl cellulose.

Matrix melt formation will be used to form uniform and semi uniform composites. In matrix melt formation, the polysaccharide component of the additive is partially molten (for semi uniform) or totally molten (for uniform) and act as matrix material. Extrusion is a very efficient way to melt a polysaccharide, such as described by Canadian Patent 2,308,537 (Huppé et al) or Canadian Patent 2,462,053 (Thibodeau et al).

Agglomerates may be manufactured in several ways. They may be prepared by tumble growth agglomeration. Agglomerates may also be made by pressure agglomeration. A useful pressure agglomeration process is extrusion. Other agglomeration techniques are described exhaustively by Pietsch (*Agglomeration Processes: Phenomena, Technologies, Equipment*, Wiley-VCH, 2002, ISBN 3-527-30369-3).

Figure 5:
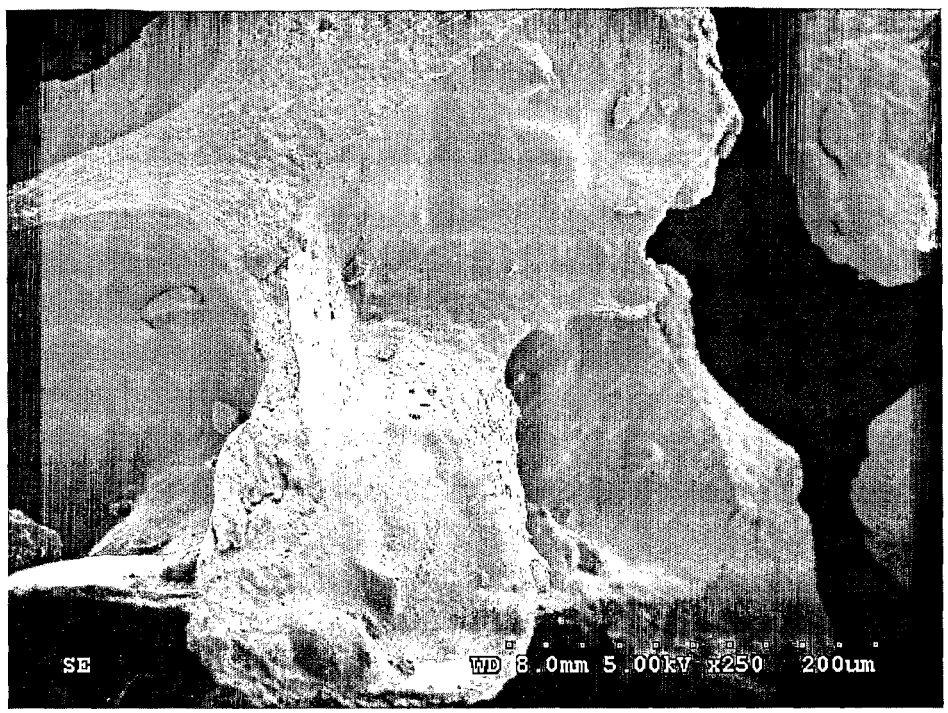
FIG. 5 illustrates a scanning electron micrograph (Magnification 250 times) of a uniform composite additive, according to yet another embodiment of the present invention.

The resulting particles are porous and sponge-like, concave or have a clustered shape, as illustrated in FIGS. 3, 5 and 1, respectively. Once formed, additive particles may be ground to specific particle size distributions. Ideally, the discrete additive particles have particle size distributions that are similar to those of the superabsorbents for which they are intended. Additives of the present invention will typically comprise particles ranging from about 150 μm to about 850 μm in size.

The additive particles of the present invention are to be discretely blended with superabsorbent polymers. The resulting absorbent composition is especially useful. Additive particles may be pre-blended with a superabsorbent polymer. Additive particles may also be blended in situ in a hygiene article (i.e. a diaper), along with fluff pulp and other components in the manufacturing process. Additives of the present invention may be used with a variety of superabsorbent polymers such as natural based SAPs, hybrid SAPs, synthetic SAPs and mixture thereof.

Natural based superabsorbent polymers may be selected from gelling polysaccharides, gelling proteins and mixtures thereof. Non-limiting examples of natural based polymers are galactomannans, glucomannans, carboxyalkyl polysaccharides, borate cross-linked galactomannans (U.S. Pat. Nos. 4,624,868 and 4,333,461 (Muller et al)), synergistic compositions of polysaccharides (Canadian Patent No. 2,426,478 (Bergeron)), cross-linked polysaccharides (Canadian Patent 2,362,006 (Couture et al), amylopectin networks (Canadian Patent 2,462,053 (Thibodeau et al)), absorbent polysaccharides nanocomposites (Canadian Patent No. 2,483,049 (Berrada et al)), guanidinated polysaccharides (Canadian Patent No. 2,519,417 (Berrada)) and modified proteins (U.S. Pat. Nos. 6,821,331 and 5,847,089 (Srinivasan et al)).

Synthetic based superabsorbent polymers are essentially made from polymerized ethylenically unsaturated hydrophilic monomers. They may be obtained by radical polymerization or radical graft polymerization. Synthetic SAPs are cross-linked, forming hydrophilic, swelling networks. Non-limiting examples of monomers which could be used to form superabsorbent polymers are acrylic acid, acrylate salts, acrylic ester, acrylic anhydride, methacrylic acid, methacrylate salts, methacrylic esters, methacrylic anhydride, maleic anhydride, maleic salts, maleate esters, acrylamide, acrylonitrile, vinyl alcohol, vinyl pyrrolidone, vinyl acetate, vinyl guanidine, aspartic acid, aspartic salts and mixtures thereof. Examples of such synthetic based superabsorbent polymers are detailed in (U.S. Pat. No. 6,087,450 (Breitbach et al); U.S. Pat. No. 5,610,220 (Klimmek et al); U.S. Pat. No. 5,612,384 (Ross et al); U.S. Pat. No. 5,453,323 (Chambers et al); and U.S. Pat. No. 5,075,344 (Johnson) as well as in Buchholz et al *Modern Superabsorbent Technology*, Wiley-VCH, 1998, ISBN: 0471194115).

Hybrid superabsorbents are superabsorbents made from graft polymerization of ethylenically unsaturated hydrophilic monomers on a natural polymer, usually a polysaccharide. Superabsorbent polysaccharide-based grafted-polymers are obtained via the grafting of an unsaturated monomer (acrylonitrile, acrylic acid, acrylamide) onto starch, or, less frequently, cellulose. The so-obtained polymers, also called "Super Slurper", have shown a water absorption ranging from 700 to 5300 g/g in deionised water, and up to 140 g/g in a 0.9% saline solution (Riccardo P. O., Water-Absorbent Polymers: A Patent Survey. J. Macromol. Sci., Rev. Macromol. Chem. Phys., 1994, 607-662 and references cited therein).

The hygiene market, and more specifically, the baby diapers market, is quite diversified. Some products, which are designated as "high tier" or "deluxe", will contain large amounts of SAP. However, in developing countries, where diaper cost is more of a concern, the SAP content is generally much lower. In fact, SAP content could range from 1.5 g to 15 g in a baby diaper. Additives of the present invention are ideally suited for use in absorbent products having a moderate to high content of superabsorbent polymers. The content of superabsorbent polymers may be calculated by determining the liquid-SAP ratio. It has been found that the additives of the present invention are especially useful with hygiene articles having a liquid-SAP ratio up to 35 ml per gram of SAP. It should be noted, however, that the liquid-SAP ratio is specific to the superabsorbent material. The liquid-SAP ratio will change with the SAP used. Best results have been observed with liquid-sap ratios ranging from about 85% to about 115% the CRC value of the used SAP.

The absorbent compositions (SAP+additive) of the present invention may be used in hygiene articles. Non-limiting examples of hygiene articles are diapers, incontinence products, airlaids, sanitary napkins, C-folds and absorbent cores.

The absorbent compositions (SAP+additive) of the present invention may be used to absorb water, aqueous solutions, saline solutions and physiological solutions, amongst other fluids. The compositions (SAP+additive) of the present invention may also be used in a method for the absorption of fluids. Non-limiting examples of fluids are water, aqueous solutions, saline solutions and physiological solutions. The method involves placing the absorbent composition in contact with the fluid.

EXPERIMENTAL

Materials

Synthetic, sodium polyacrylate superabsorbent were obtained from Stockhausen GmbH (Krefeld, Germany) and BASF (Ludwigshafen, Germany). Grade A wheat starch was obtained from Archer Daniels Midland® (Decatur, USA). Corn starch was obtained from Cargill (Minneapolis, USA). National™ Premium WT-200 bentonite was purchased from Bentonite Performance Minerals® (Denver, USA). Terra Alba, gypsum was obtained from United States Gypsum Company® (Chicago, USA). Clinoptilolite zeolite was obtained from Cycletrol® (Carson City, USA).

Eirich Intensive Mixer

An Eirich Intensive Mixer type RO2 from Maschinenfabrik Gustav Eirich, (Hardheim, Germany) was used to agglomerate the polysaccharide and the inorganic component.

Twin-Screw Extruder

Two twin screw extruders were used. A Coperion Werner & Pfleiderer ZSK58 MC (Stuttgart, Germany), and a Baker-Perkins Twin-screw extruder MPF-50D from APVBaker Invensys, (Grand Rapids, USA) were used to manufacture the composite.

Figure 7:
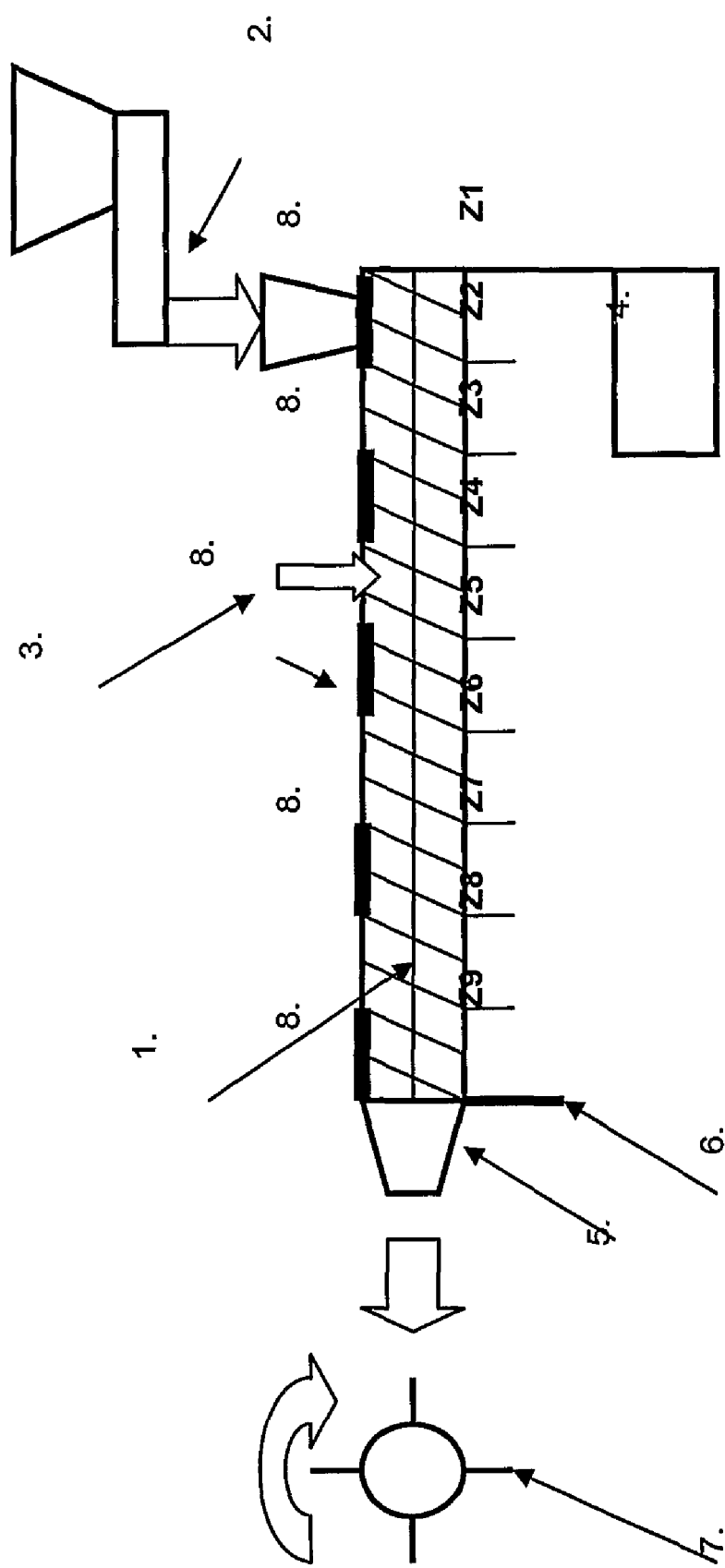
FIG. 7 illustrates a side elevation view of a twin screw extruder (TSE) that may be used to make the composite additives of the present invention.

As illustrated in FIG. 7, the motor powered (4) extrusion lines (1) were composed of feeders, either volumetric or gravimetric, (2) feeding premixed solid components or each component individually into a solid entry port (8), a liquid injection port for water addition (3), a die plate (5) and a die-face pelletizer (7). Both twin screw extruders have 9 temperature control zones, noted as Z1, Z2, Z3, Z4, Z5, Z6, Z7, Z8 and Z9 and a pressure transducer (6).

The Baker-Perkins twin-screw extruder configuration starts with a zone of conveying elements, followed by zones of pumping elements, kneading elements and ends with pumping elements just before a die plate of either 6 or 9 mm die opening.

The Coperion twin-screw extruder configuration starts with a zone of conveying elements, followed by zones of pumping elements, kneading elements and ending with pumping elements. The extrudate is further fed into a single screw ESA150 attached with a EGR pelletizer mounted with a die plate of 3 mm die opening.

It should be noted that Buss-Kneader extruders could also be used. Extrudates may be cooled. Extrudates exiting the extruders could be pumped for pressure build-up or final moisture removal. This can be done by various systems, such as single screw extruders or gear pumps. The extrusion can also be done on longer or shorter machines. Extruders having a length/diameter ratio (L/D ratio) ranging from about 15 to about 50 could be used. The extruder may have a side feeder for feeding additional ingredients downstream. This side feeder may also act as a devolatalizer removing the moisture from the ingredients or removing entrapped gases. The position of the degassing side feeder can be from about 12 L/D ratio to about 24 L/D ratio. A side feeder can also be installed in the vicinity to the exit of the extruder to remove excess moisture. This is usually done after the water is added to the product. An upstream vent, prior to injection of water, may be used to allow air to escape.

Convection Oven

Samples were dried in a Lab tray drier TY 2, National Drying Machinery Company, (Philadelphia, USA).

High Speed Chopper

Urschel Comitrol model 3600 with 3B030030 blade was used (Valparaiso, USA).

Grinder

A Quaker City (Straub® Co, Philadelphia, USA) grinding mill model F-4 was used to grind the produced additives samples.

Sieve Shaker

When indicated, samples were sieved using a Tyler Ro-Tap™ test sieve shaker. Another sieve shaker, referred as vibrating siever was used; Kason model K24-3-SS, (Scarborough, Canada).

Test Methods

As discussed in Modern Superabsorbent Polymer Technology (Buchholz F. L. and Graham A. T. Eds., Wiley-VCH, New York, 1998, section 4.6.1. Swelling Capacity: Theory and Practice, p. 147), several methods of measurement may be used in order to characterize the swelling capacity of a polymer. In the field of superabsorbents, the Gravimetric Swelling Capacity [also called the Free Swell Capacity (FSC)] and the Centrifuge Capacity [also called the Centrifuge Retention Capacity (CRC)] are recommended methods. The FSC and the CRC are used to compare the swelling capacities of the obtained absorbent products.

Tea bags for FSC and CRC measurements

Tea bags (10×10 cm) are made from heat sealable Ahlstrom™ filter paper (16.5±0.5) g/m².

FSC Measurements

The Free Swell Capacity (FSC) in a 0.9% NaCl solution is determined in accordance with the recommended test method 440.2-02 from EDANA.

CRC Measurements

The Centrifuge Retention Capacity (CRC) in a 0.9% NaCl solution was determined in accordance with the recommended test method 441.2-02 from EDANA.

Particle Rewet

Rewet is a measurement especially useful in the hygiene industry. To better reflect the influence of the additive of the present invention on this characteristic, the rewet test was adapted for particles. In a 50 ml centrifuge test tube, 0.600 g of SAP was carefully weighed. A precise quantity of additive was weighed and blended with the superabsorbent polymer. Saline solution (18 ml) was added to the absorbent composition (liquid SAP ratio of 30 ml/g) and the composition let to absorb for precisely 30 minutes. About 4.5-5.0 g of filter paper was carefully weighed and placed on a Plexiglas plate. Over the filter paper, a 26 gsm nonwoven (Carded-Thermobonded Polypropylene from Industrias Maquin S. A., Huejotzingo, Mexico) was placed over the filter papers. Alternatively, other acquisition distribution layers may be used. Swollen absorbent composition is poured on the nonwoven fabric. An aluminum piston, exerting a pressure of 0.7 Psi on the absorbent composition, was by placed on the nonwoven fabric. The filter paper was allowed to absorb for precisely 2 minutes, then the filter papers were carefully weighed. The particle rewet is the amount of fluid absorbed by the filter paper ($W_{paper\ wet} - W_{paper\ dry}$).

Scanning Electron Micrographs

Scanning electron micrographs were recorded using a Hitachi® S 3000N scanning electron microscope. Samples were placed on two-sided adhesive paper, glued to an aluminum plate. Any non-glued particles were removed with an air jet. A thin (about 10 nm) gold layer was then applied to the surface of the glued sample by a sputter coater. The surface was then scanned and recorded.

EXAMPLES

Example 1

Starch, Zeolite, Clay Composite Additive Semi-Uniform Morphology

A mixture comprised of 70% wheat starch, 24% bentonite and 6% zeolite was compounded using the Baker Perkins twin-screw extruder with a die opening of 9 mm. The solid composition was mixed and wetted with 30% tap water. The mixture was fed with a volumetric feeder and extruded at a throughput of 31 kg/h. Cooling was applied to the extruder using tap water, and all zones were 16° C. Zone 1 was not used. The screw speed was set at 200 RPM. The agglomerated material exited the extruder at about 75° C. with a die pressure of about 270 psig. The motor load was at about 30-40%. This indicates that frictional heat was generated in the process.

The extrudates were then placed in a convection oven at 85° C. for at least 3 hours and ground. The ground product was sieved using a RO-Tap sieve shaker. Samples larger than 30 Mesh were discarded, as well as samples smaller than 40 Mesh, in order to avoid any particle size effect interference on performances of the absorbent composition. The additives produced were characterized as described in Example 4. SEM of this sample was illustrated in FIGS. 3 and 4. The porosity of the additive can be observed from these figures.

Example 2

Starch, Zeolite, Clay Composite Additive Uniform Morphology

A mixture comprising of 70% wheat starch, 24% of bentonite and 6% of zeolite was compounded using the Baker Perkins twin-screw extruder with a die opening of 6 mm. The solid composition was mixed and wetted with 26% tap water. The mixture was fed with a volumetric feeder and extruded at a throughput of about 18 kg/h. Temperature zones were: $Z_1$ zone was not used, $Z_2$=32° C., $Z_3$=38° C., $Z_4$=48° C., $Z_5$=65° C., $Z_6$=82° C., $Z_7$=93° C., $Z_8$=104° C., $Z_9$=115° C. The screw speed was set at 100 RPM. The agglomerated material exited the extruder about 131° C. The motor load was about 40%.

Figure 6:
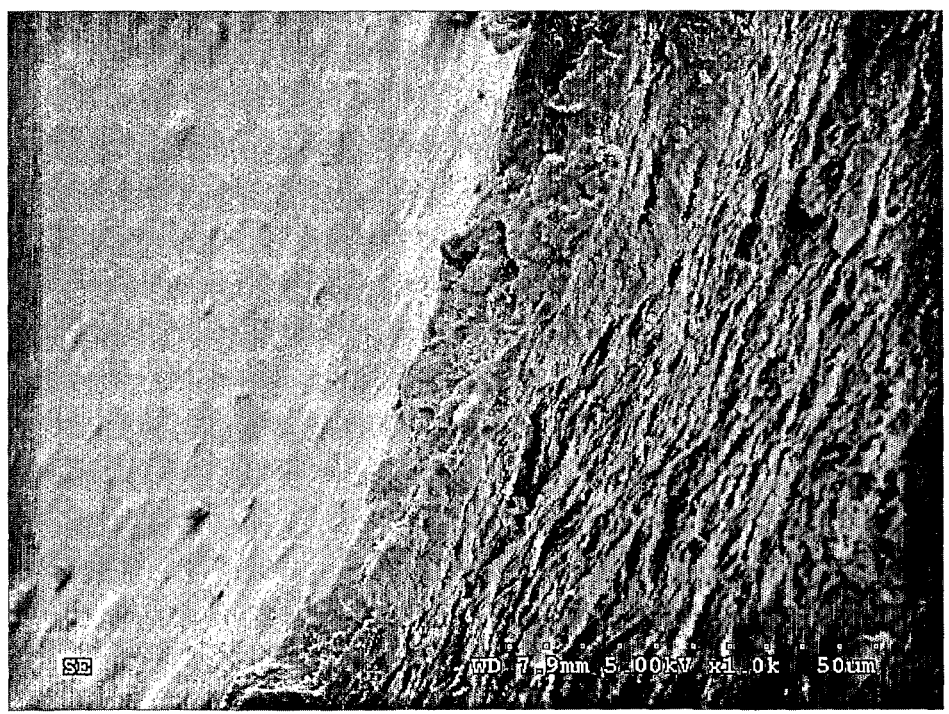
FIG. 6 illustrates a scanning electron micrograph (Magnification 1,000 times) of the uniform composite additive shown in FIG. 5.

The extrudates were then placed in a convection oven at 85° C. for at least 3 hours and ground using a high-speed chopper. The ground product was sieved using a RO-Tap sieve shaker. Samples larger than 30 Mesh were discarded, as well as samples smaller than 40 Mesh, in order to avoid any particle size effect interference on performances of the absorbent composition The additives produced were characterized as described in Example 4. SEM of this sample was illustrated in FIGS. 5 and 6. The porosity of the additive can be observed from these figures, as well as their concave design.

Example 3

Starch, Zeolite, Clay Composite Additive Agglomerated Morphology

A mixture comprising of 70% corn starch, 24% of bentonite and 6% of zeolite was compounded using the Coperion twin-screw extruder. The mixture was fed with a volumetric feeder at a rate of 194 Kg/h and 26% of cold water added. Corn starch, bentonite and zeolite were fed separately in the Coperion extruder with gravimetric feeders at the rate of 300 lbs/h, 103 lbs/h and 26 lbs/h, respectively. Tap water was injected at a rate of 155 lbs/hr, corresponding to a 26% addition. The extrusion throughput was about 580 lbs/hr. Temperature zones were: $Z_1=15°$ C., $Z_2=34°$ C., $Z_3=35°$ C., $Z_4=35°$ C., $Z_5=34°$ C., $Z_6=36°$ C., $Z_7=41°$ C., $Z_8=43°$ C., $Z_9=47°$ C. The screw speed was set at 220 RPM. The agglomerated material exited the extruder about 35° C. The motor load was about 15%.

Figure 2:
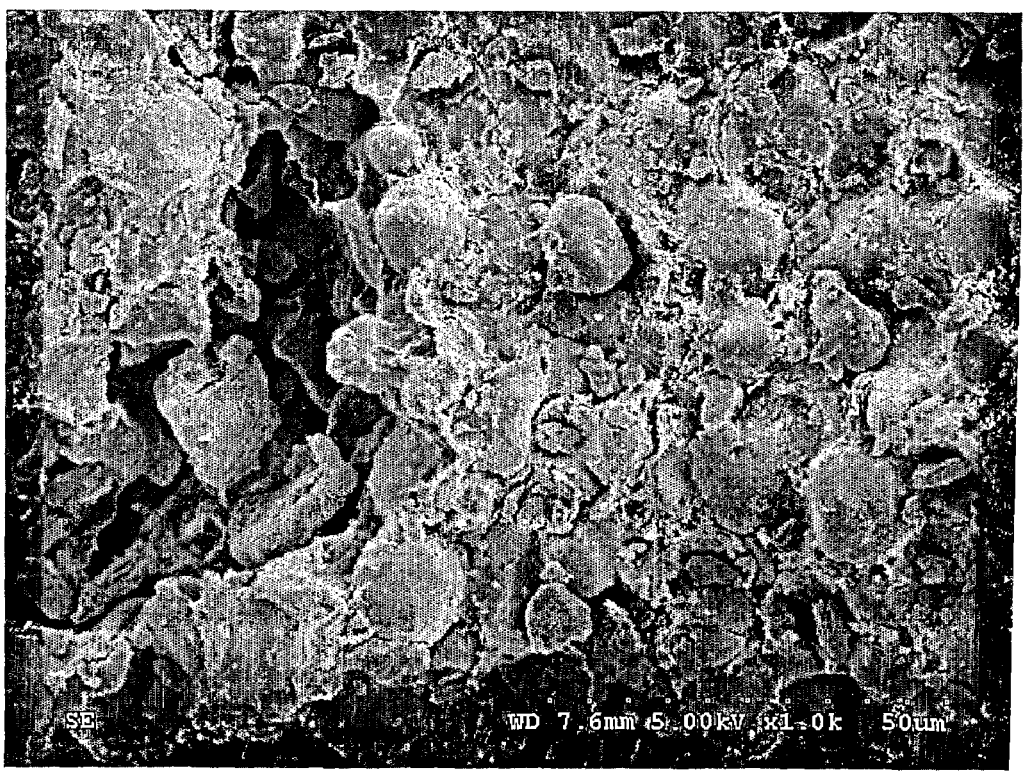
FIG. 2 illustrates a scanning electron micrograph (Magnification 1,000 times) of the agglomerated composite additive shown in FIG. 1.

The extrudates were then placed in a convection oven at 85° C. for at least 3 hours and ground using a high-speed chopper. The ground product was sieved using a RO-Tap sieve shaker. Samples larger than 30 Mesh were discarded, as well as samples smaller than 40 Mesh, in order to avoid any particle size effect interference on performances of the absorbent composition. The additives produced were characterized as described in Example 4. SEM of this sample was illustrated in FIGS. 1 and 2. The clustered design of the additive can be observed from these figures.

Example 4

Absorbent Compositions

Figure 8:
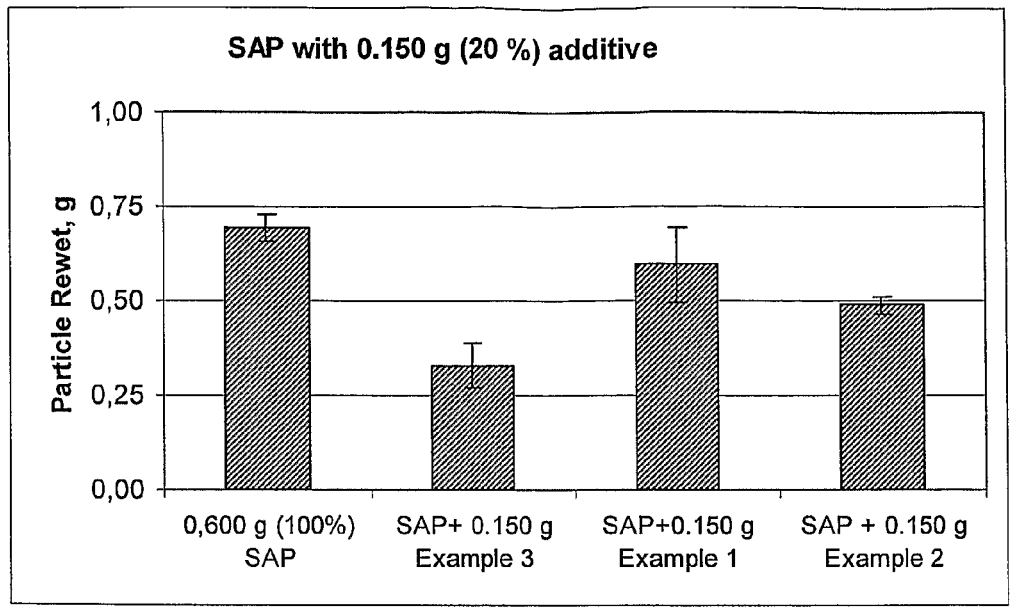
FIG. 8 is a bar graph showing the relative rewet performances of absorbent compositions comprising additives (20%) in accordance with an embodiment of the present invention.
Figure 9:
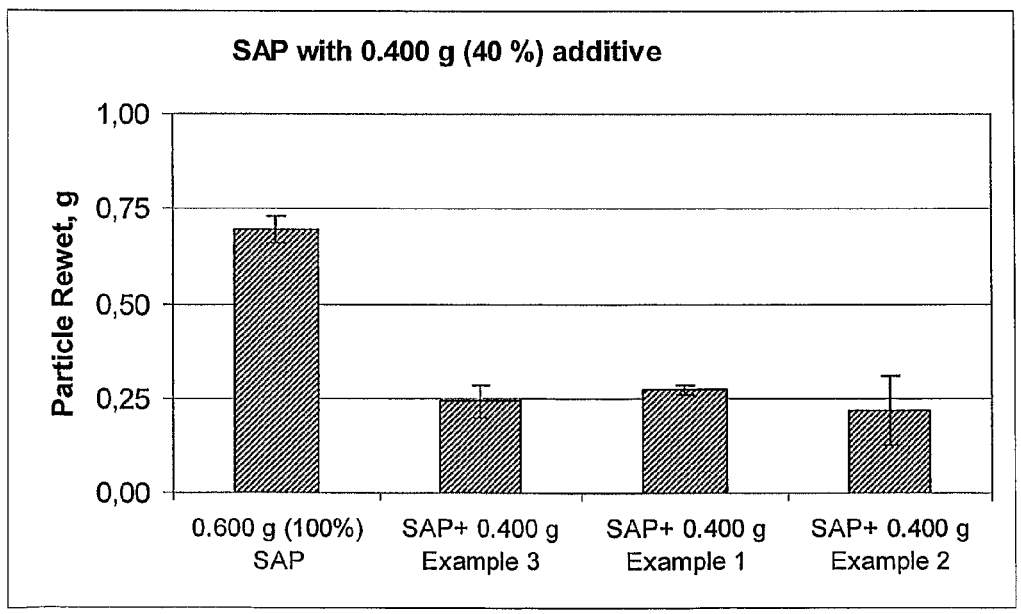
FIG. 9 is a bar graph showing the relative rewet performances of absorbent compositions comprising additives (40%) in accordance with another embodiment of the present invention.

Synthetic superabsorbent polymer (BASF Hysorb 8650) was carefully weighed (0.600 g). To this mass, 0.150 g (20%) or 0.400 g (40%) of additives particles were added and blended. Particle rewet values are reported in FIGS. 8 and 9. CRC was also characterized, as shown in Table 1. As it may be appreciated, the agglomerated morphology improves significantly particle rewet of superabsorbent polymer. However, matrix melt formation yields a better CRC.

TABLE 1

CRC performances in Examples 1 to 3 for additives at various concentrations

| SAP Content | Additive and content | CRC (g/g) |
| --- | --- | --- |
| 100% SAP |  | 33.2 |
| 80% SAP | 20% Example 3 | 26.8 |
| 80% SAP | 20% Example 1 | 26.8 |
| 80% SAP | 20% Example 2 | 27.4 |
| 60% SAP | 40% Example 1 | 20.3 |
| 60% SAP | 40% Example 3 | 20.4 |
| 60% SAP | 40% Example 2 | 21.4 |

Example 5

Starch Zeolite Agglomerates with a Binder

A dry powder is prepared by physically blending of 50% of starch, 49% of zeolite. One (1) % of carboxymethylcellulose (CMC) was swelled with 30% of aqueous solution, and then compacted. The obtained paste was dried overnight in an oven at 60° C. The resulting pellet was ground with a Quarker City mill and sieved, keeping only particles having a size ranging from 150 µm to 600 µm. Finally, this powder was blended with superabsorbent polymers (Stockhausen Favor SXM 9145) with additives charge varying from 10% to 20%. The powder performances of the so-obtained formulation were reported in Table 2.

TABLE 2

Performance of SAP-Additive blends, with the Example 5 agglomerated additive

| Agglomerates (% w/w) | SAP (% w/w) | FSC | CRC |
| --- | --- | --- | --- |
| 0 | 100 | 52.1 | 31.7 |
| 10 | 90 | 50.3 | 31.7 |
| 15 | 85 | 50.1 | 31.0 |
| 20 | 80 | 48.3 | 30.7 |

Example 6

Starch Gypsum Clay by Tumble Growth Agglomeration

A mixture comprising of 80% wheat starch, 18% of bentonite and 2% of gypsum was micropelletized using an Eirich Intensive Mixer. The following agglomeration procedure was applied: 1500 g of the mixture is fed into the mixer, the agitation is set at 855 RPM and 643 g of water is then added to the mixture over a period of 30 seconds. This agitation is maintained for 1 minute after the water addition. After the 1 minute period, the agitation speed is increased to 1765 RPM for another minute, then the agitation speed is increased to 3490 RPM and 700 g of the mixture is fed in the mixer over a period of 1 minute. Once all the mixture is added, the agitation is maintained for 1 minute at 3490 RPM. The resulting moist agglomerated mixture is sieved and the −850 µm/+150 µm fraction is then dried in an oven at 60° C. to bring the moisture down to 7%. Table 3 shows the performances of various blends of SAP (Favor SXM 9145) and the dried agglomerated mixture (−850 µm/+150 µm fraction).

TABLE 3

Performances of blends of SAP and starch, clay, gypsum agglomerates

| Agglomerates (% w/w) | SAP (% w/w) | FSC | CRC |
| --- | --- | --- | --- |
| 0 | 100 | 52.1 | 31.7 |
| 10 | 90 | 48.0 | 28.3 |
| 15 | 85 | 45.8 | 26.3 |
| 20 | 80 | 43.8 | 26.0 |

The invention claimed is:

1. An additive comprising a discrete composite particle for discrete blending with a superabsorbent polymer, said discrete composite particle comprising 40%-90% of a starch component and an inert inorganic component, said starch component and said inert inorganic component remaining distinct on a micrometric level and wherein when said additive is blended with the superabsorbent polymer the blend has a lower rewet capacity at 0.7 psi than the superabsorbent particle not blended with said additive.

2. The additive of claim 1, wherein said starch component is selected from the group consisting of unmodified starches, modified starches, amylopectin, modified amylopectin, amylose, modified amylose and mixtures thereof.

3. The additive of claim 2, wherein said starch component is selected from the group consisting of starch granules, pregelatinized starches, glass-like starches, waxy starches, cross-linked starches, hydroxyalkylated starches, alkylated starches and mixtures thereof.

4. The additive of claim 3, wherein said starch granules have a diameter ranging from 1 μm to 60 μm.

5. The additive of claim 2, wherein said starch component is obtained from sources selected from the group consisting of wheat, maize, buckwheat, potato, waxy starches, cassaya, sorghum, millet, oat, arrowroot, barley, beans, peas, rice, rye and mixtures thereof.

6. The additive of claim 1, wherein said discrete composite particle comprises from about 1% to about 40% of said inert inorganic component.

7. The additive of claim 1, wherein said inert inorganic component has a particle size ranging from about 10 μm to about 150 μm.

8. The additive of claim 1, wherein said inert inorganic component is selected from the group consisting of swelling clays, zeolites, silica gel, insoluble salts and mixture thereof.

9. The additive of claim 8, wherein said swelling clays are selected from the group consisting of smectites, hectorites, bentonites, montmorillonites, Laponites™, celites, illites and mixture thereof.

10. The additive of claim 1, wherein said discrete composite particle comprises a morphology selected from the group consisting of uniform, semi-uniform and agglomerated.

11. The additive of claim 1, further comprising a binder.

12. The additive of claim 1, wherein said discrete composite particle has a size ranging from about 150 μm to about 850 μm.

13. The additive of claim 1, wherein said discrete composite particle is obtained by pressure agglomeration, tumble growth agglomeration or matrix melt formation.

14. The additive of claim 13, wherein said discrete composite particle is obtained by extrusion.

15. An absorbent composition comprising: a) the additive of claim 1 and b) a discrete superabsorbent polymer characterized by a centrifuge retention capacity of at least 15 g/g.

16. The absorbent composition of claim 15, wherein said superabsorbent polymer is selected from the group consisting of natural superabsorbents, synthetic superabsorbents, hybrid superabsorbents and mixtures thereof.

17. The absorbent composition of claim 16, said composition being characterized in that when comprised of a weight ratio of 40:80 additive:superabsorbent polymer, the absorbent composition has a rewet capacity of about $\frac{1}{3}^{rd}$ and retains at least 60% of the centrifuge retention capacity observed with a comparative composition containing 100% of the superabsorbent polymer.

18. A hygiene article comprising the absorbent composition of claim 15.

19. A method of absorbing fluids comprising, contacting a an article comprising the absorbent composition of claim 15 with a fluid selected from the group consisting of water, aqueous solutions, saline solutions and physiological solutions for a time sufficient to absorb at least a portion of the fluid into the absorbent composition.

20. A method for making the absorbent composition of claim 1, comprising: a) blending a polysaccharide component and an inert inorganic component; b) at least partially melting said polysaccharide component to form a melt; c) drying the melt to form a dried melt; and d) grinding the dried melt to produce composite particles that when blended with a superabsorbent polymer characterized by having centrifuge retention capacity of at least 15 g/g forms an blended superabsorbent mixture having a lower rewet capacity than the superabsorbent polymer alone.

21. A method for making the absorbent composition of claim 1, comprising a) blending a polysaccharide component and an inert inorganic component to form a blend; b) agglomerating the blend to form an agglomerate; c) drying the agglomerate to form a dried agglomerate; d) grinding the dried agglomerate to produce composite particles that when blended with a superabsorbent polymer characterized by having centrifuge retention capacity of at least 15 g/g forms an blended superabsorbent mixture having a lower rewet capacity than the superabsorbent polymer alone.

\* \* \* \* \*